US010246997B2

(12) United States Patent
Serres et al.

(10) Patent No.: US 10,246,997 B2
(45) Date of Patent: Apr. 2, 2019

(54) SAMPLE TESTING DEVICE AND FLUID PUMPING INSTALLATION COMPRISING SUCH A TESTING DEVICE

(71) Applicant: PCM TECHNOLOGIES, Levallois-Perret (FR)

(72) Inventors: Stephanie Serres, Ingrandes-sur-Loire (FR); Gregoire Crotte, Champtoce sur Loire (FR); Eric Perret, Champtoce sur Loire (FR)

(73) Assignee: PCM TECHNOLOGIES, Levallois-Perret (FR)

( * ) Notice: Subject to any disclaimer, the term of this patent is extended or adjusted under 35 U.S.C. 154(b) by 192 days.

(21) Appl. No.: 15/220,045

(22) Filed: Jul. 26, 2016

(65) Prior Publication Data
US 2017/0030190 A1 Feb. 2, 2017

(30) Foreign Application Priority Data

Jul. 27, 2015 (FR) ...................... 15 57169

(51) Int. Cl.
*E21B 49/08* (2006.01)
*E21B 47/01* (2012.01)
*G01N 3/00* (2006.01)
*G01N 17/04* (2006.01)

(52) U.S. Cl.
CPC .......... *E21B 49/08* (2013.01); *E21B 47/011* (2013.01); *G01N 3/00* (2013.01); *G01N 17/046* (2013.01); *G01N 2203/0242* (2013.01); *G01N 2203/0244* (2013.01); *G01N 2203/04* (2013.01); *G01N 2203/0664* (2013.01)

(58) Field of Classification Search
None
See application file for complete search history.

(56) References Cited

U.S. PATENT DOCUMENTS

| 2,433,718 | A | | 12/1947 | Teplitz | |
|---|---|---|---|---|---|
| 2,664,744 | A | | 1/1954 | Bilhartz et al. | |
| 2,994,778 | A | * | 8/1961 | Marsh | G21H 5/02 250/303 |
| 3,123,157 | A | * | 3/1964 | Graham | E21B 27/005 166/319 |
| 4,483,397 | A | * | 11/1984 | Gray | E21B 23/03 166/117.5 |
| 4,928,760 | A | | 5/1990 | Freitas | |
| 5,095,977 | A | * | 3/1992 | Ford | E21B 41/02 166/113 |
| 5,150,065 | A | * | 9/1992 | Luna | G01N 17/00 324/700 |
| 7,025,138 | B2 | | 4/2006 | Kurkjian et al. | |
| 2012/0074969 | A1 | | 3/2012 | Snelling et al. | |

* cited by examiner

Primary Examiner — Jill E Culler
(74) Attorney, Agent, or Firm — Patzik, Frank & Samotny Ltd.

(57) ABSTRACT

A device for testing samples of material in a fluid upstream of a pump of a fluid pumping installation and a pumping installation comprising such a device, the device comprising: a casing having one inlet opening for the fluid and one outlet opening for the fluid, the outlet opening fixed to the pump; and a perforated cartridge to contain the samples of material to be tested, the perforated cartridge being arranged in the casing between the inlet opening and the outlet opening.

17 Claims, 3 Drawing Sheets

SAMPLE TESTING DEVICE AND FLUID PUMPING INSTALLATION COMPRISING SUCH A TESTING DEVICE

RELATED APPLICATIONS

This invention claims priority to French patent application No. FR 15 57169, filed Jul. 27, 2015, the entirety of which is hereby incorporated by reference.

FIELD OF THE INVENTION

The present invention lies in the field of installations for pumping industrial fluids such as hydrocarbons and water.

BACKGROUND OF THE INVENTION

The invention relates to the dimensional and physico-chemical characterization of any material, used in a progressive cavity pump, which could have its mechanical, physical, chemical, and dimensional properties altered over time by the pumped fluid.

This characterization may, for example, provide an understanding of the swelling of the elastomer forming the stator under the environmental conditions in which the pump is to be used, in order to achieve the best rotor-stator engagement. When this engagement is insufficient, hydraulic pump efficiency is degraded. Conversely, when this engagement is too tight, the friction caused by the excessive engagement heats the elastomer, leading to a change in its mechanical properties. This change results in premature aging, degradation, and loss of functional properties of the pump or even destruction of the stator.

It is known to characterize the materials used in a progressive cavity pump by "off-site" or "ex situ" tests. However, the environmental conditions existing downhole (pressure, temperature, chemical composition, acidity . . . ), sometimes several kilometers from the surface, are not really known and are difficult to reproduce in the laboratory. To overcome this disadvantage, some tests such as aging tests are performed with fluid samples pumped from a well, pipe, pipeline, tank, etc. However, many components (gas, volatile materials) are lost during the transfer of the pumped fluid from its original environment to the characterization laboratory, rendering the tests more or less approximate. In addition, the existing environmental conditions downhole (pressure, temperature, chemical composition, acidity) vary as the well matures. These environmental conditions also vary from one well to another.

As a result, characterizing materials by using such "ex situ" tests is unsatisfactory because it is too approximate.

SUMMARY OF THE INVENTION

The purpose of the present invention is to provide a device enabling a more realistic characterization of the mechanical, physicochemical, and possibly dimensional evolution of materials used in downhole conditions (bathing in a multiphase mixture, temperature, and pressure).

To this end, the object of the invention is a device for testing samples of material, suitable for attachment upstream of a pump of a fluid pumping installation, characterized in that the device comprises:
 a casing having at least one inlet opening for the fluid and at least one outlet opening for the fluid, the outlet opening being intended to be fixed to the pump;
 a perforated cartridge intended to contain the samples of material to be tested, the perforated cartridge being arranged in the casing between the inlet opening and the outlet opening.

Advantageously, this device allows obtaining test samples from the flow of pumped fluid. These samples are thus tested in the same environment as the pump. In particular, these samples are exposed to the same fluid as the pump components—a fluid composed of multiphase mixtures. They are subjected to the same pressure and temperature conditions as the pump components.

This device thus allows testing samples under conditions that are closer to the actual conditions downhole.

According to some embodiments, the sample testing device comprises one or more of the following features:

The casing has a cylindrical wall, and a closed end face in line with the outlet opening, the cylindrical wall having a first solid portion and a second portion provided with the at least one inlet opening, the first portion being adjacent to the closed end face (16) so as to form a reservoir intended to contain a portion of the fluid to be pumped.

Advantageously, the device allows removing from the well a portion of the fluid to be pumped. The fluid may be poured into a transport container for samples. This maintains the samples in the downhole multiphase mixture as they are transported to the sample analysis laboratory. This fluid is more suitable for maintaining the samples closer to their true aging.

The perforated cartridge comprises:
  a perforated sleeve,
  two closure plates having a diameter greater than the diameter of the perforated sleeve, the closure plates each being provided with a central opening;
  a rod arranged in the perforated sleeve and passing through the central openings of the closure plates, and fastening members for attaching each closure plate against an end of the perforated sleeve.
  the perforated cartridge further comprises at least one intermediate plate provided with a central opening traversed by the rod, and at least two spacers fitted onto the rod on each side of the intermediate plate.

The closed end face is formed by a cap fixed to the first portion, the testing device further comprising a bar having one end secured to the cap and one end provided with a threaded bore, the rod being screwed into the threaded bore of the bar.

Advantageously, this system allows simple removal of the cartridge from the casing by detaching the cap.

It comprises a deformation sensing device for detecting the deformation of a sample of material over time, the deformation sensing device comprising:
  a housing with one open face and provided with holes for the passage of the fluid to be pumped, the housing being intended to contain the sample of material to be tested, and
  a measurement sensor suitable for measuring the deformation of the sample of material, the measurement sensor being arranged next to the open face of the housing.

The perforated cartridge comprises a sample elongation device for stretching samples of material.

The perforated cartridge comprises at least one device for compressing samples of material.

The perforated cartridge comprises intermediate plates fitted onto the rod and spacers fitted onto the rod, each spacer being interposed between two intermediate plates to form a compartment for storing samples of material.

The fastening members comprise a thread provided at least at each end of the rod, and at least two securing nuts.

The closure plates and/or the intermediate plates and/or the at least one spacer are perforated.

The present invention also relates to a fluid pumping installation comprising a pump and a device for testing samples of material that provides features mentioned above.

BRIEF DESCRIPTION OF THE DRAWINGS

The invention will be better understood from reading the following description given solely by way of example and with reference to the figures in which.

DETAILED DESCRIPTION OF THE INVENTION

Figure 1:
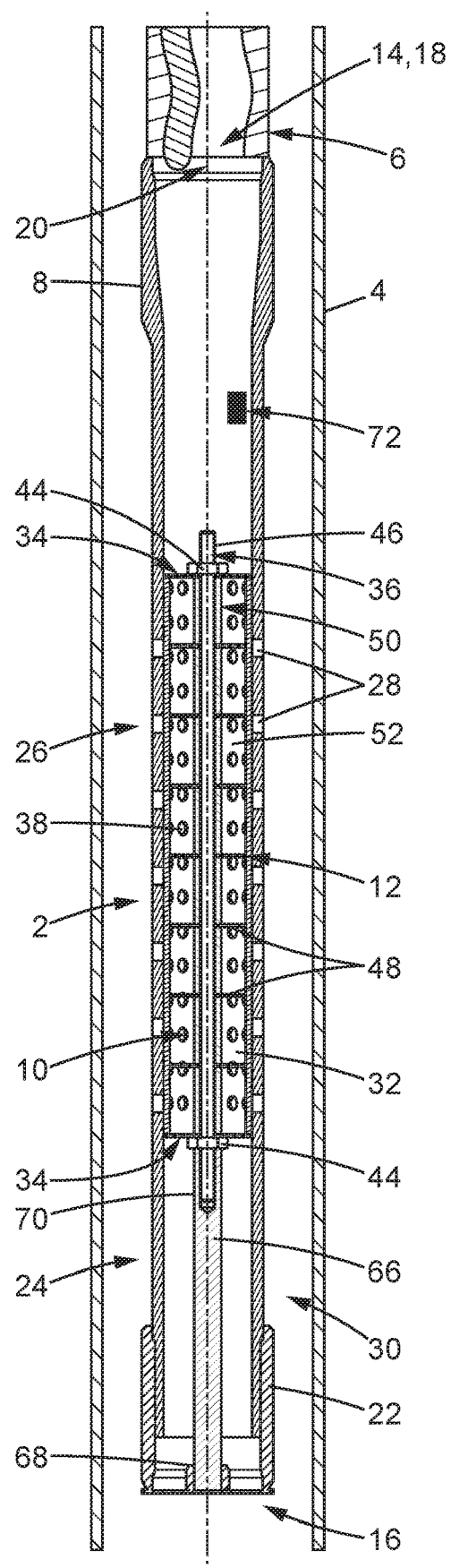
FIG. 1 is a schematic partial axial section view of the testing device according to the invention, when the device is installed in a pipe of a pumping installation.

While this invention is susceptible of embodiment in many different forms, there is shown in the drawings and will herein be described in detail several specific embodiments, with the understanding that the present disclosure is to be considered merely an exemplification of the principles of the invention and the application is limited only to the appended claims.

By convention, in the following description the terms "top", "bottom", "lower", "upper", "right", and "left" are used relative to the testing device being installed in a well as shown in FIG. 1, but are in no way limiting.

Referring to FIG. 1, the testing device 2 of the invention is intended to be installed in the stabilizing casing 4 of a hydrocarbon or water pumping installation that uses a progressive cavity pump 6. The testing device 2 is suitable for testing materials such as metals or elastomers.

The testing device 2 comprises a casing 8 and a perforated cartridge 10 arranged in the casing 8.

The casing 8 has the shape of a cylinder. It has a cylindrical wall 12, an upper end face 14, and a lower end face 16.

The upper end face 14 comprises an outlet opening 18 for fluid. This upper end face 14 is intended to be attached to the suction opening 20 of the progressive cavity pump.

The lower end face 16 is closed. In particular, a cap 22 is fastened, for example by screwing, to the cylindrical wall 12 of the casing. The cylindrical wall 12 has a solid lower portion 24 and an upper portion 26 in which inlet openings 28 for the pumped fluid are formed. The lower portion 24 is adjacent to the closed end face 16. The lower portion 24 and the cap 22 form a reservoir 30 intended to contain the fluid to be pumped.

The perforated cartridge 10 comprises a perforated sleeve 32, two closure plates 34 each detachably fastened against the perforated sleeve, and a threaded rod 36 arranged in the perforated sleeve.

In the exemplary embodiment of the invention illustrated in FIG. 1, the perforated sleeve 32 is cylindrical. It is provided with through-holes 38 distributed across its entire surface.

Figure 2:
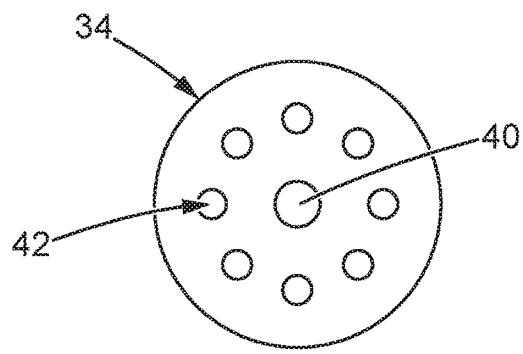
FIG. 2 is a schematic front view of a closure plate of the testing device illustrated in FIG. 1.

Referring to FIG. 2, the closure plates 34 have a diameter greater than the diameter of the perforated sleeve 32. They are each provided with a central opening 40 and with through-holes 42 allowing the passage of the fluid to be pumped.

The rod 36 is mounted in the perforated sleeve 32 and in the central openings 40 of the cartridge closure plates. Securing nuts 44 are screwed onto each end of the rod 36 to bring the closure plates 34 into abutment against the perforated sleeve 32.

The thread 46 of the rod and the securing nuts 44 form fastening members that fasten each closure plate 34 against an end of the perforated sleeve 32.

The perforated cartridge 10 further comprises intermediate plates 48 fitted onto the rod 36 and spacers 50 also fitted onto the rod 36.

The intermediate plates 48 are identical to the closure plates 34 except that they are smaller in diameter than the perforated sleeve 32. Spacers 50 are interposed between two intermediate plates 48 or between a closure plate 34 and an intermediate plate 48. The spacers 50 consist, for example, of tube sections. The length of each spacer 50 is defined according to the size of the sample to be arranged between two plates 34, 48. The space defined between two adjacent plates 34, 48 forms a compartment 52.

Figure 3:
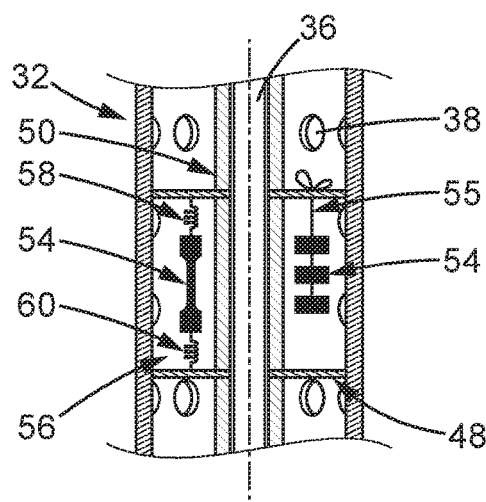
FIG. 3 is a schematic axial section view of a first example of a portion of the testing device according to the invention.

Referring to FIG. 3, the samples of materials to be tested 54 are, for example, fastened to a plate 34, 48 by a wire 55 or a cable, or are fastened between two plates 34, 48 by wires attached to the through-holes 42. Advantageously, this type of attachment holds the samples 54 away from the walls of the perforated sleeve 32 while ensuring complete immersion in the pumped fluid.

The perforated cartridge 10 may comprise a sample elongation device 56 for stretching a sample of material. This elongation device 56 comprises, for example, a first spring 58 secured to an intermediate plate 48 or to a closure plate 34, and a second spring 60 secured to an intermediate plate 48 or to an adjacent closure plate 34. The sample of material to be tested 54 is intended to be fastened to the first and second springs. An elongation force can thus be applied to the samples of material 54 in order to perform stress test characterization, for example dumbbell test specimens with 5% elongation.

Figure 4:
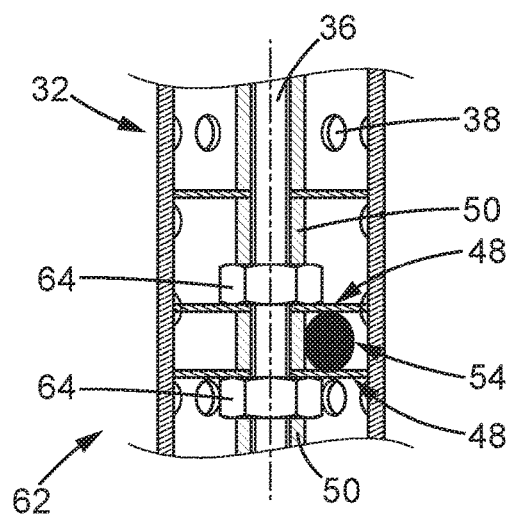
FIG. 4 is a schematic axial section view of a compression device of the testing device according to the invention.

In a variant represented in FIG. 4, the perforated cartridge 10 comprises a device 62 for compressing a sample of material. This compression device 62 comprises, for example, two intermediate plates 48 fitted onto the rod 36 on each side of the samples to be tested 54 and two compression nuts 64 screwed onto the rod 36, each against an intermediate plate 48, so as to compress the sample(s) of material 54 interposed between two intermediate plates 48. A spacer 50 is provided on the upper compression nut 64, then a new intermediate plate 48 is placed on the spacer 50.

Referring to FIG. 1, the testing device 2 of the invention further comprises a bar 66 of which one end 68 is integral with the cap 22 and one end 70 is provided with a threaded axial bore. The lower end of the threaded rod 36 is screwed into the threaded bore provided at end 70 of the bar 66. Advantageously, when the cap 22 is detached from the lower portion 24 of the casing, the perforated cartridge 10 is removed from the casing at the same time by means of the bar 66.

The bar 66 has a length such that the upper closure plate 34 is located above the inlet openings 28 of the casing, to ensure optimum immersion of the samples of material 54.

Figure 5:
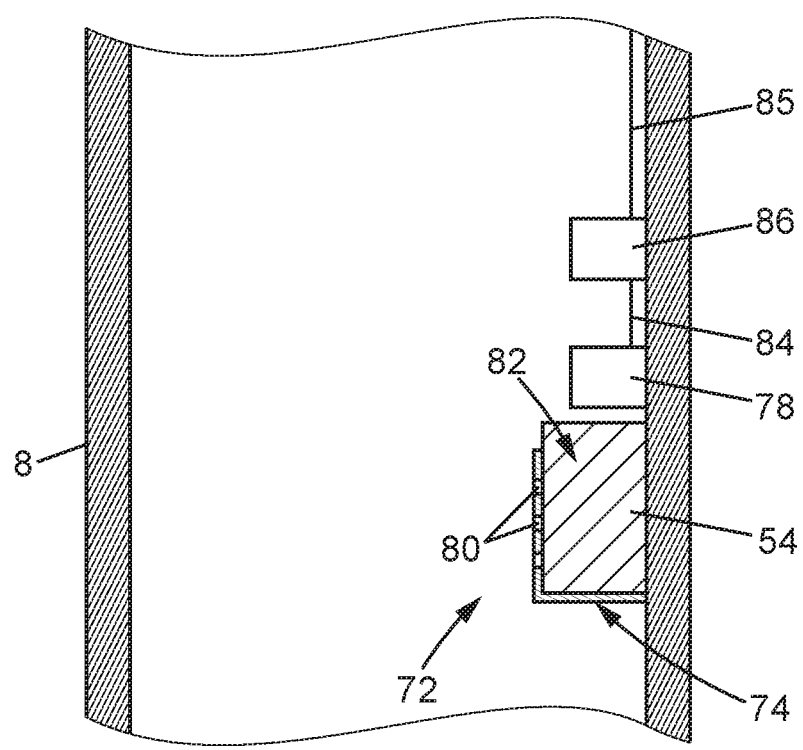
FIG. 5 is a schematic view of a device for measuring the deformation of an elastomer, fixed to the testing device.

Preferably, the testing device 2 also comprises a deformation sensing device 72 for detecting the deformation of a sample of material 54 over time. This device is illustrated in FIGS. 1 and 5. It allows obtaining measurements of the deformation of an elastomer over time.

The deformation sensing device 72 comprises a housing 74 intended to receive a sample of material 54 to be tested and a measurement sensor 78 suitable for measuring the deformation of the sample of material 54.

The housing 74 is arranged on the inner face of the cylindrical wall 12. It is provided with holes 80 allowing the passage of the fluid to be pumped. The upper face 82 of the housing is completely open to the inner space of the casing.

The measurement sensor 78 is also fixed to the inner face of the cylindrical wall, in line with the open upper face 82 of the housing. The measurement sensor 78 is, for example, a strain gauge, a strain gauge bridge (Wheatstone bridge), or a displacement sensor.

The sample of material to be tested 54 is of a size corresponding to the size of the housing 74, so that when it expands or retracts, this only occurs in a direction the measurement sensor 78 can detect.

The measurement sensor 78 is connected by a wired connection 84 to a electronic processing and signal amplification unit 86. This unit is connected by a wired connection 85 to a data processing unit located on the surface, outside the well. Alternatively, the measurement data are transmitted to the surface by the unit 86 via a wireless connection such as, for example, a radiofrequency link.

In FIG. 1, the casing 8 has the shape of a right circular cylinder. Alternatively, the directrix of the cylinder may have any other shape, for example a square shape.

Alternatively, the casing 8 does not comprise a reservoir 30. In this case, either the cylindrical wall is perforated, or it is solid and the inlet opening(s) are provided on the lower end face.

Alternatively, the perforated sleeve 32 is made of wire mesh.

Alternatively, the perforated cartridge 10 comprises a different number of intermediate plates and spacers. In another alternative, the perforated cartridge 10 does not comprise an intermediate plate. It provides a single compartment. In this case, the rod may only be threaded at its ends.

Alternatively, the progressive cavity pump 6 is replaced by a peristaltic pump.

In FIG. 1, the inlet openings 28 permitting the entry of fluid into the casing are circular. According to a variant (not shown), these inlet openings are slots, for example longitudinal slots.

To conduct a test using the testing device according to the invention, the samples of material 54 are prepared so that they have the size or shape suitable for conducting a test in situ or ex situ, for example, typically in a format such as dumbbell test specimens, test bars, peel specimens, etc. They are prepared in the laboratory. All initial properties of the samples of material 54 are measured. These samples of material 54 are then placed in the perforated cartridge 10. In particular, a series of samples of material 54 is deposited for example in the perforated sleeve 32 on the closure plate 34. A spacer 50 is then inserted onto the rod 36 and lodged against the closure plate 34. An intermediate plate 48 is then inserted onto the rod 36 and placed on the spacer 50, forming a compartment 52. The samples of material 54 are thus immobilized between the closure plate 34 and the intermediate plate 48. Each compartment 52 comprises samples of the same type or of a type specific to the compartment, for example a type of elastomer. This helps to properly differentiate the nature of each sample.

When the rotor of the progressive cavity pump 6 is rotated in the stator, this draws the fluid to be pumped. The fluid passes through the inlet openings 28 of the casing. Much of the drawn fluid passes through the perforated cartridge 10 and bathes the test samples 54 contained therein. The drawn fluid then leaves the casing 8 via the outlet opening 18 and enters the progressive cavity pump 6.

The casing is mounted on the same production line as the progressive cavity pump 6 using elastomers or any other material that may undergo immediate change or change over time in its mechanical, physicochemical, or dimensional properties due to the nature of the pumped fluid, so that the fluid passing through the perforated cartridge 10 has physicochemical, temperature, and pressure characteristics that are equivalent to the fluid passing through the progressive cavity pump.

The invention claimed is:

1. A device for testing samples of material in a fluid, upstream of a pump of a fluid pumping installation, the device comprising:
 a casing having at least one inlet opening for the fluid and at least one outlet opening for the fluid, the outlet opening fixed to the pump, wherein the casing has a cylindrical wall, and a closed end face in line with the outlet opening, the cylindrical wall having a first solid portion and a second portion provided with the at least one inlet opening, the first portion being adjacent to the closed end face so as to form a reservoir to contain a portion of the fluid to be pumped; and
 a perforated cartridge to contain the samples of material to be tested, the perforated cartridge being arranged in the casing between the inlet opening and the outlet opening.

2. The device according to claim 1, wherein the closed end face is formed by a cap fixed to the first portion, the device further comprising a bar having one end integral with the cap and one end provided with a threaded bore, the rod being screwed into the threaded bore of the bar.

3. The device according to claim 1, comprising a deformation sensing device for detecting the deformation of a sample of material over time, the deformation sensing device comprising:
 a housing with one open face and provided with holes for the passage of the fluid to be pumped, the housing to contain the sample of material to be tested, and
 a measurement sensor suitable for measuring the deformation of the sample of material, the measurement sensor being arranged next to the open face of the housing.

4. The device according to claim 1, wherein the perforated cartridge comprises a sample elongation device for stretching samples of material.

5. The device according to claim 1, wherein the perforated cartridge comprises at least one device for compressing samples of material.

6. A fluid pumping installation, comprising a pump and device according to claim 1.

7. A device for testing samples of material in a fluid, upstream of a pump of a fluid pumping installation, the device comprising:
 a casing having at least one inlet opening for the fluid and at least one outlet opening for the fluid, the outlet opening fixed to the pump; and
 a perforated cartridge to contain the samples of material to be tested, the perforated cartridge being arranged in the casing between the inlet opening and the outlet opening, wherein the perforated cartridge comprises:

a perforated sleeve, two closure plates having a diameter greater than the diameter of the perforated sleeve, the closure plates each being provided with a central opening;

a rod arranged in the perforated sleeve and passing through the central openings of the closure plates, and fastening members for attaching each closure plate against an end of said perforated sleeve.

8. The device according to claim 7, wherein the casing has a cylindrical wall, and a closed end face in line with the outlet opening, the cylindrical wall having a first solid portion and a second portion provided with the at least one inlet opening, the first portion being adjacent to the closed end face so as to form a reservoir to contain a portion of the fluid to be pumped.

9. The device according to claim 7, wherein the perforated cartridge further comprises at least one intermediate plate provided with a central opening traversed by the rod, and at least two spacers fitted onto the rod on each side of the intermediate plate.

10. The device according to claim 7, wherein the closed end face is formed by a cap fixed to the first portion, the device further comprising a bar having one end integral with the cap and one end provided with a threaded bore, the rod being screwed into the threaded bore of the bar.

11. The device according to claim 7, comprising a deformation sensing device for detecting the deformation of a sample of material over time, the deformation sensing device comprising:

a housing with one open face and provided with holes for the passage of the fluid to be pumped, the housing to contain the sample of material to be tested, and a measurement sensor suitable for measuring the deformation of the sample of material, the measurement sensor being arranged next to the open face of the housing.

12. The device according to claim 7, wherein the perforated cartridge comprises a sample elongation device for stretching samples of material.

13. The device according to claim 7, wherein the perforated cartridge comprises at least one device for compressing samples of material.

14. The device according to claim 7, wherein the perforated cartridge comprises intermediate plates fitted onto the rod and spacers fitted onto the rod, each spacer being interposed between two intermediate plates to form a compartment for storing samples of material.

15. The device according to claim 7, wherein the fastening members comprise a thread provided at least at each end of the rod, and at least two securing nuts.

16. The device according to claim 7, wherein the closure plates and/or the intermediate plates and/or the at least one spacer is perforated.

17. A fluid pumping installation, comprising a pump and device according to claim 7.

\* \* \* \* \*